United States Patent [19]
Guerra

[11] Patent Number: 5,796,487
[45] Date of Patent: Aug. 18, 1998

[54] DARK FIELD, PHOTON TUNNELING IMAGING SYSTEMS AND METHODS FOR OPTICAL RECORDING AND RETRIEVAL

[75] Inventor: John M. Guerra, Concord, Mass.

[73] Assignee: Polaroid Corporation, Cambridge, Mass.

[21] Appl. No.: 671,708

[22] Filed: Jun. 28, 1996

[51] Int. Cl.$^6$ .................................................. G01B 11/24
[52] U.S. Cl. ............................................. 356/376; 356/373
[58] Field of Search ..................................... 356/376, 371, 356/373

[56] References Cited

U.S. PATENT DOCUMENTS

| | | | |
|---|---|---|---|
| 4,681,451 | 7/1987 | Guerra et al. | 356/373 |
| 5,349,443 | 9/1994 | Guerra | 356/371 |
| 5,442,443 | 8/1995 | Guerra | 356/371 |
| 5,539,197 | 7/1996 | Courjon et al. | 250/216 |

Primary Examiner—Frank G. Font
Assistant Examiner—Zandra V. Smith
Attorney, Agent, or Firm—Joseph Stecewycz

[57] ABSTRACT

A dark-field imaging system and method that employs photon tunneling to optically encode and decode information at full-field and in real-time or substantially real-time for recording and retrieval purposes. The system is particularly useful for high density information storage in media in which submicron scattering sites are formed. The system comprises an illumination section for illuminating a surface of an optical recording media with an evanescent field. A collecting section is positioned with respect to the illuminated surface to channel radiant energy converted from the evanescent field by the scattering sites to unbound energy propagating away from the surface. Various embodiments of the illumination section are disclosed including the use of a bulk optic prismatic element, the forward aplantic element of a compound microscope objective, diffracting gratings, and optical waveguides. In each embodiment the collection section and illumination section may be completely optically and, thus, physically uncoupled.

28 Claims, 16 Drawing Sheets

DARK FIELD, PHOTON TUNNELING IMAGING SYSTEMS AND METHODS FOR OPTICAL RECORDING AND RETRIEVAL

CROSS REFERENCE TO RELATED APPLICATIONS

This application is related to the three concurrently-filed U.S. patent applications entitled, "Dark field, photon tunneling imaging systems and methods," "Dark field, photon tunneling imaging probes," and "Dark field, photon tunneling imaging systems and methods for measuring flying height of read/write heads," all by John M. Guerra.

BACKGROUND OF THE INVENTION

1. Field of the Invention

This invention in general relates to the fields of imaging and metrology of surfaces and, more specifically, to systems and methods that use evanescent field illumination in real-time, whole-field imaging and measurement of surfaces at low magnification and at wide angle.

2. Description of the Prior Art

Photon tunneling microscopy for measuring and visualizing submicron surface topographic features is known. Descriptions of the use of photon tunneling microscopy are contained, for example, in: Harrick, N. J., "Use of Frustrated Total Internal Reflection to Measure Film Thickness and Surface Reliefs," *J. Appl. Phys.*, 1962. 33: p. 321; McCutchen, C. W., "Optical Systems for Observing Surface Topography by Frustrated Total Internal Reflection and by Interference," *The Review of Scientific Instruments*, Vol. 35, p. 1340–45, 1964; Guerra, J. M., "Photon tunneling microscopy," in Proceedings from Surface Measurement and Characterization Meeting, Hamburg, SPIE Vol. 1009, September 1988, pp. 254–62, U.S. Pat. No. 4,681,451 entitled, "Optical proximity imaging method and apparatus," issued to Guerra, J. M. and Plummer, W. T. Jul. 21, 1987; U.S. Pat. No. 5,349,443 entitled, "Flexible transducers for photon tunneling microscopes and methods for making and using same," issued to Guerra, J. M. Sep. 20, 1994; and U.S. Pat. No. 5,442,443 entitled, "Stereoscopic Photon Tunneling Microscope," issued to Guerra, J. M. Aug. 15, 1995.

Harrick, McCutchen, Guerra/Plummer, and Guerra disclose whole-field reflected evanescent light microscopes where the sample is not transilluminated nor scanned, but rather is illuminated by an evanescent field from an unrestricted total reflection surface at the object plane of an epi, or reflected light, illuminator. Here, the sample can be opaque or transparent, thick or thin, and can be viewed in real-time with high energy throughput. Such microscopes are very sensitive to smooth surfaces because of their use of the exponentially-varying amplitude of the evanescent field in the vertical direction to sense very small surface height variation. On the other hand, rougher surfaces scatter light back into the microscope, which decreases contrast and sensitivity. Also, the deeper topography is rendered as bright, because these areas penetrate the evanescent field to a small degree so that the epi-illumination is nearly totally reflected. The difficulty in detecting and measuring small changes in bright scenes limits the observable topographic depths to about ¾ of the illuminating wavelength (which is the wavelength in air divided by the index of refraction, n, and the sine of the angle of incidence, θ). Further, the illumination and imaging optics are coupled because the objective serves as the condenser as well. This limits in a practical sense the use of such instruments to the availability of suitable commercial objectives, magnifications, fields of view, and numerical aperture. In addition, it is difficult, because of the coupling of imaging and illumination optics, to affect the polarization, phase, incident angle, and direction of the illumination. This, in turn, restricts the ability to maximize the tunneling range, increase lateral resolution, or tunnel through less rare media such as water in biological applications.

Devices in which evanescent light from transilluminated samples is scattered into objective pupils are described in G. J. Stoney, "Microscopic Vision," Phil. Mag. p. 332, at 348–49, 1896; Surface contact microscope, Taylor & Francis; Ambrose, E. J., "A Surface Contact Microscope for the Study of Cell Movements," Nature, Nov. 24, 1956, vol. 178; Ambrose, E. J., "The Movements of Fibrocytes," Experimental Cell Research, Suppl. 8, 54–73 (1961); Temple, P. A., "Total internal reflection microscopy: a surface inspection technique," Applied Optics, Vol. 20, No. 15, Aug. 1981; and D. Axelrod, in *Fluorescence Microscopy of Living Cells in Culture, Part B*, ed. D. L. Taylor and Y-L. Wang, (Academic Press, New York, 1989), Chap. 9.

Stoney, Ambrose, Temple, and Axelrod disclose optical evanescent light field microscopes in which the light that enters the objective pupil is evanescent field light that has been scattered from a sample surface. However, in all of these microscopes, the sample is transilluminated, with the illumination incident at beyond the critical angle such that the evanescent field from the sample surface is received. It is then necessary that the sample be transparent at optical frequencies, or is made thin enough to be transparent.

Scanning devices which rely on scattered evanescent field light are described in: Fischer, U. Ch., Dürig, U. T., and Pohl, D. W., "Near-field optical scanning microscopy in reflection," Appl. Phys. Lett., Vol. 52, No. 4, pp. 249–251 25, Jan. 1988. Fischer et al. disclose a near-field optical microscope in which the sample is not transilluminated but is rather illuminated in reflected light. Further, this reflected light is in the form of an evanescent field from a dielectric plate into which light is launched at greater than the critical angle, by means of a coupled prism, so that it undergoes multiple total internal reflections, giving rise to the evanescent field. However, Fisher et al. restrict the evanescent field with an aperture in a metal opaque coating on the total reflection surface of the dielectric plate. This aperture is smaller than the wavelength of light so that an improvement in lateral resolution beyond the normal Abbe limit is achieved, but at the cost of having to scan the aperture relative to the sample to build up an image. A further cost is that energy throughput is very low, making extension to analytical optical techniques such as spectroscopy problematic.

Devices which utilize transillumination of transparent samples are described in R. C. Reddick, R. J. Warmack, and T. L. Ferrell, "New form of scanning optical microscopy," Phys. Rev. B 39, 767–70 (1989). Reddick et al. disclose transillumination of thin and transparent samples with evanescent light, but the entrance pupil in Reddick et al is not an objective in the conventional microscopy sense. Rather it is an optical fiber that is scanned over the sample, close to the sample surface. Thus there is a loss of flux throughput, and vertical resolution is limited by the mechanism that controls the vertical position of the fiber relative to the sample. A means of scanning in the xy plane is also required, preventing true real-time whole-field imaging.

While the art describes a variety of devices that utilize evanescent field illumination for investigating surface characteristics, there remains a need for improvements that offer advantages and capabilities not found in presently available instruments, and it is a primary object of this invention to provide such improvements.

Another object is to provide a means of optical data recording and reading with very high signal to noise performance and very high storage density.

It is another object of the invention to extend the use of photon tunneling imaging to scattering surfaces.

Another object is to extend the use of photon tunneling microscopy to rough surfaces by increasing the detectable vertical tunneling range.

Another object is to detect light scattered out of the evanescent field by a sample surface in reflected light, rather than in transillumination.

Another object is to decouple the illumination optics and optical path from the imaging/collection optics when using the evanescent field to illuminate a surface.

Another object is to allow wider fields of view and a larger range of magnifications than with current practices.

Another object is to allow greater control over the illumination incident angle, polarization, wavelength, coherence, and phase.

Another object is to provide devices for evanescent field illumination that are thin enough to allow use of standard working distance objectives.

A further object is to reduce sensitivity to optical inhomogeneity in the sample surface relative to topography.

Other objects of the invention will be obvious, in part, and, in part, will become apparent when reading the detailed description which follows.

SUMMARY OF THE INVENTION

This invention generally relates to the fields of surface imaging and fine detail measurement through the application of evanescent field illumination and, in particular, to methods and apparatus by which bound evanescent field illumination may be converted by scattering into propagating light that is subsequently collected and imaged for optical encoding and decoding for storage and retrieval purposes. An optical storage media is selectively provided with scattering sites in the form of bumps or disturbances by which information is encoded or decoded. The media is illuminated by an evanescent field and scatters the bound energy in accordance with its scattering sites. The scattered light is collected and imaged where the intensity variation of the image varies in accordance with the surface scattering sites, their location, and the proximity of a scattering site to the evanescent field. Image intensity may be correlated with calibrated geometry to provide a means for encoding the intensity variations as variations in gray tones. The intensity of the image may be mapped to a gray tone image in the form of a signal which bears tone density corresponding directly to the presence or absence of a scattering sites. The gray tone signal thereafter may be used as an input to a number of display possibilities including digital monitors, 3-D oscilloscopes, or other forms of display.

In the absence of a scattering site, light is reflected totally outside of the entrance pupil of the imaging system and thus creates a dark field. Hence, the name "dark-field" photon tunneling. In the normal photon tunneling microscope (PTM), the evanescent field is converted into propagating light by refraction into smooth surfaces and away from the entrance pupil of the microscope. In the absence of a sample surface, the light is reflected totally into the microscope entrance pupil, for a bright field. In addition, the dark field PTM is different from normal dark field microscopy in that the illumination is evanescent light, and not propagating light. Sample features get brighter against a dark background as they get closer to the microscope, so height information is obtained. In normal dark field, sample feature brightness depends on their size and slope, rather than their height.

In accordance with a further feature of the invention, the imaging optics and illumination optics are decoupled so that advantages are enjoyed in flexibility of light control as well as image magnification and numerical aperture.

In general, the inventive imaging systems are best used on media that can carry scattering or rougher sites compared with their unperturbed configuration since very smooth surfaces scatter very little light energy into the pupil. On the other hand, these systems are less sensitive to the optical properties of the media because the conversion of the evanescent field is largely by scattering, rather than by diffraction/refraction. Also, the imaging and illumination optics and optical paths are easily decoupled so that the polarization, phase, incident angle, and wavelength of the illumination is easily controlled. Finally, because the imaging optics are separate and do not require a numerical aperture of one or greater, a much larger range of magnifications, fields of view, and numerical apertures are available commercially.

BRIEF DESCRIPTION OF THE DRAWINGS

The structure and operation of the invention, together with other objects and advantages thereof, may best be understood by reading the detailed description in connection with the drawings in which unique reference numerals have been used throughout for each part and wherein.

DETAILED DESCRIPTION

This invention generally relates to the fields of surface imaging and fine detail measurement through the application of evanescent field illumination and, in particular, to methods and apparatus by which bound evanescent field illumination may be converted by scattering into propagating light that is subsequently collected and imaged for optical encoding and decoding for purposes of storage and retrieval. A number of different dark-field, photon tunneling imaging systems are described along with different ways of providing the necessary evanescent field illumination in an uncoupled manner. Various other applications relating to magnetic disk flying height measurement, optical surface measurement, as well as optical storage are also described. To understand the optical storage applications, however, it will first be necessary to be introduced to dark field photon imaging systems and their properties, which will now be discussed.

Figure 1:
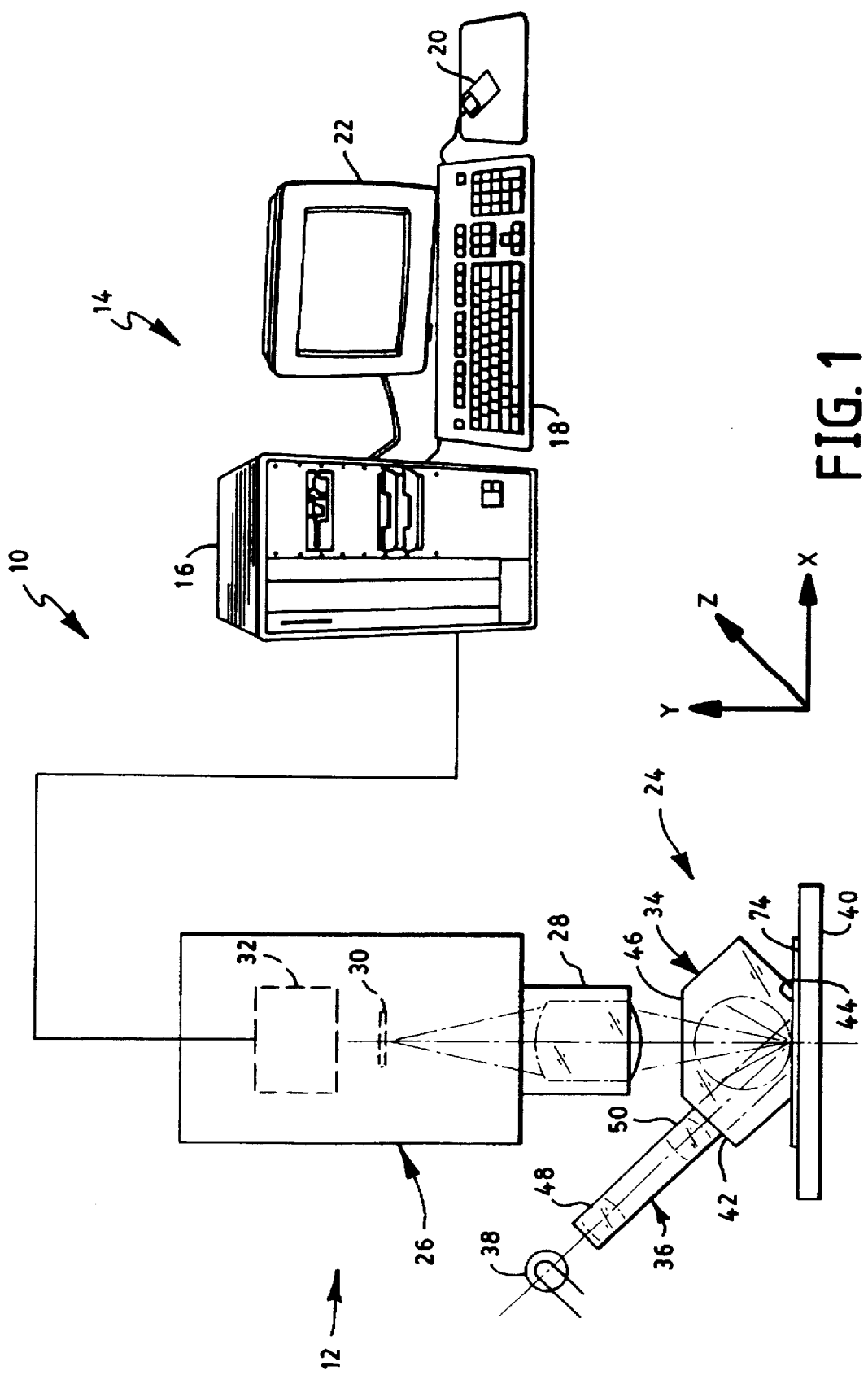
FIG. 1 is a diagrammatic partially elevational and partially perspective view of a dark-field, photon tunneling system of the invention.

Reference is now made to FIG. 1 which shows a dark field, photon tunneling imaging system of the invention designated generally at 10. As will be seen system 10 is particularly suitable for visualizing and measuring at full field and in real time the microtopographic features of roughened or other surfaces that have small scattering features but otherwise appear smooth. In particular, system 10 and other embodiments of the invention are suitable for use in measuring the surface characteristics of aircraft and space vehicle structures, paint, paper, and fabrics. Because of the lighting and detecting mechanisms employed in dark field imaging, it is possible to decouple the illumination and imaging paths so that probes remote from the imaging sections can be contrived.

As seen in FIG. 1, system 10 comprises an illumination and image formation section 12 and an image processing and display section 14. Section 14 may be any well-known general purpose computer or work station 16 having a CPU, RAM memory, hard and floppy drives, input devices such as a keyboard 18 and mouse 20, and color display monitor such as at 22. Preferably, computer 16 has 16 or more megabytes of RAM and is otherwise equipped with high throughput data and video buses. The internal video card is preferably one selected with two or more megabytes of on-board memory and is capable of generating 32-bit or more colors for high tone resolution. Internal signal and image processing programs may be stored on computer 16's internal hard drive and transferred to RAM in the usual way for any processing needs required.

Figure 2:
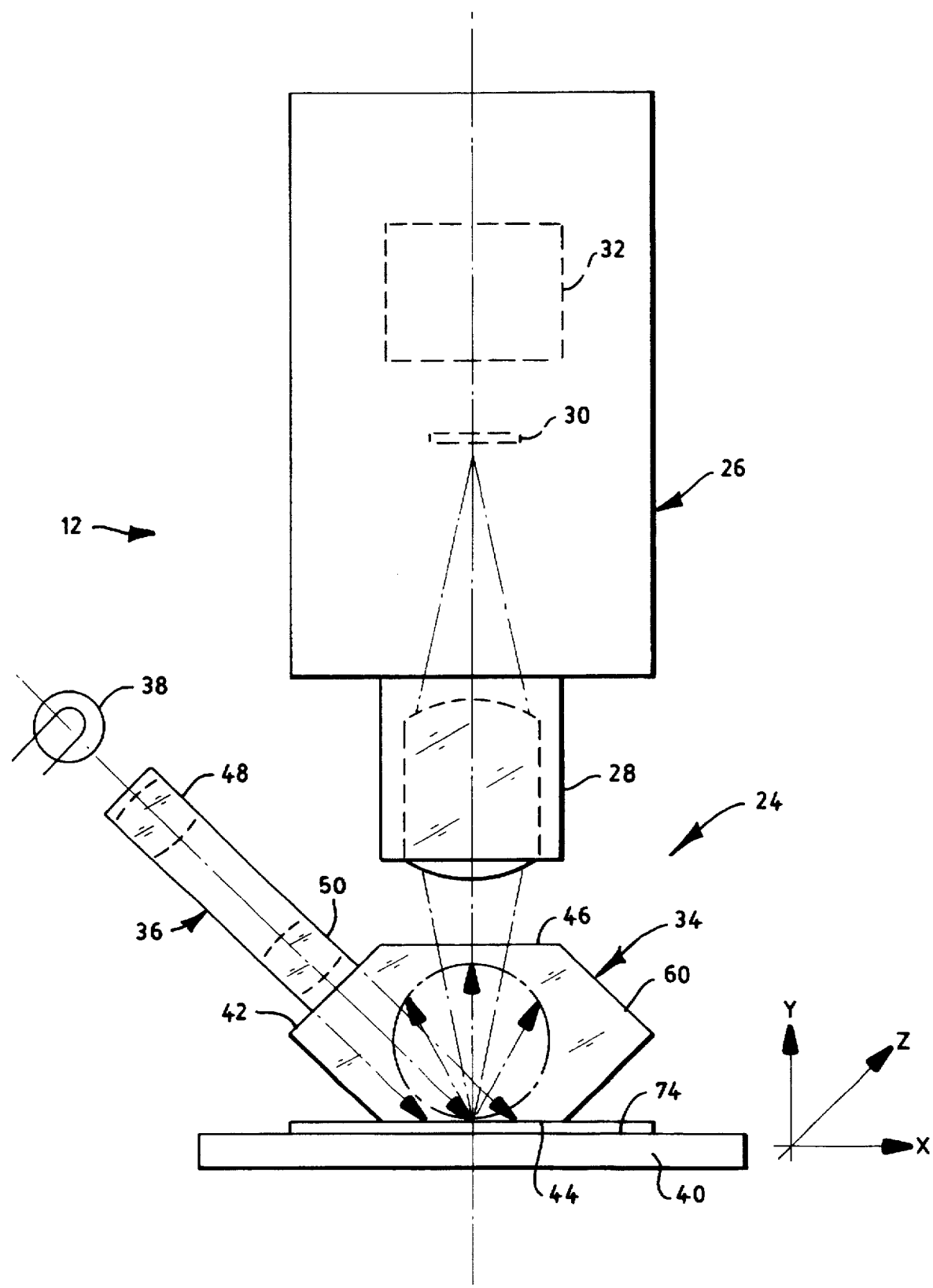
FIG. 2 is an enlarged, diagrammatic, elevational view of a portion of the system shown in FIG. 1.

As best seen in FIGS. 1 and 2, illumination and imaging section 12 comprises an optical head 24 for illuminating and contacting the surface of a sample to be visualized and measured, and a video camera 26 for collecting and imaging propagating radiation scattered from a sample's surface.

Video camera 26 may be any suitable conventionally available type of the desired spatial and tonal resolution. Preferably, video camera 26 is a wide-angle type and may have a magnifying or slightly minifying objective lens 28. Objective lens 28 may alternatively be a zoom lens of appropriate tele- to wide-angle design.

Located at the plane of best focus of objective lens 28 is a photo detector 30, which may be a conventional CCD or vidicon tube. Video signals generated from photo detector 30 may be processed on board camera 26 via a resident chip 32 for that purpose or may be sent via an appropriate board resident in a slot in computer 16. In either event, camera 26 and computer 16 may be configured in well-known manners so that video signals may be digitized to generate digital images that can change for display on monitor 22 at real-time rates or nearly real-time rates.

Optical head 24 comprises a bulk optic, prismatic dielectric body 34, having, among others, a light entering facet 42, a sample contacting facet 44, and a light emitting facet 46. Optically coupled to facet 40 is an illumination section comprising a collimating optical section 36 consisting of a tube in which are resident suitable collimating optics in the form of spaced apart lenses 48 and 50. An illumination source 38 is provided, and radiation emitted by source 38 is directed through facet 42 to facet 44.

Figure 4A:
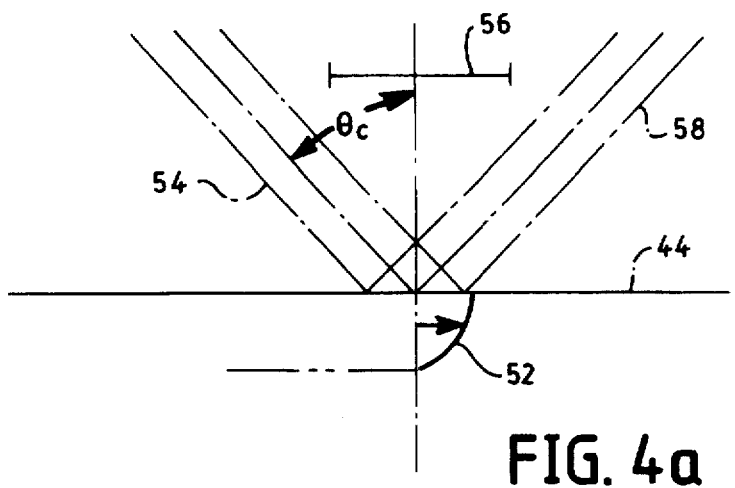
FIGS. 4a–4d diagrammatic views illustrating how light may be scattered into the entrance pupil of the detection section of the embodiments of the invention depending on whether or not there is a scattering sample present and the corresponding images that may be observed on the display section.

As best seen in FIGS. 2 and 4a, light in transmissive dielectric body 34 is incident at an angle equal to or greater than the critical angle $\theta_c$ so that it totally reflects at the interface with a less dense medium such as air or water, i.e., at facet 44. It is understood that dielectric body 34 can be transmissive over all or any part of the electromagnetic spectrum, including but not limited to ultra-violet, infrared, or even x-ray and millimeter wave extremes, depending on the application. Although the incident light is shown to be a collimated beam, it need not be, and in fact imaging resolution improves if the incident light is less coherent.

As seen in FIG. 4a, an evanescent field 52 arises at the boundary between facet 44 and the lower index medium opposite it (usually air, but this medium may also be water or another low index medium). Evanescent field 52 has an amplitude that decays exponentially with distance from the surface of facet 44. The strength of evanescent field 52 is given by:

$$E_{evanescent} = E_0 \exp\left(-\frac{z}{d_p}\right)$$

where $E_0$ is the amplitude of the electric field associated with the photon in the medium comprising body 34 and, $d_p$ is the penetration depth in the less dense medium at which $E_0$ decreases to $E_0/e$ and where:

$$d_p = \frac{\lambda_1}{2\pi(\sin^2\theta - n_{21}^2)^{1/2}}$$

and $\lambda_1$ is the wavelength in the denser medium, $\theta$ is the incidence angle, and $n_{21}$ is the ratio of denser to lower indices of refraction at the boundary of facet 44. The actual penetration depth, where $E_0$ falls to the limit of detectability, is dependent on these variables as well as both the photo-detector sensitivity and the sample optical properties, and is typically approximately $0.75\lambda$. However, the evanescent field, however small in intensity, can exist sensibly for tens of wavelengths, if the parameters on the last above equation are optimized.

As is well-known, evanescent field 52 penetrates normal to the surface of facet 44 to the depth indicated above. Consequently, it extends beyond the physical boundary of facet to a predetermined depth and can be interrupted by a sample placed in close proximity to facet 44. The action of doing so will now be explained with reference to FIGS. 4a to 4d.

Figure 4B:
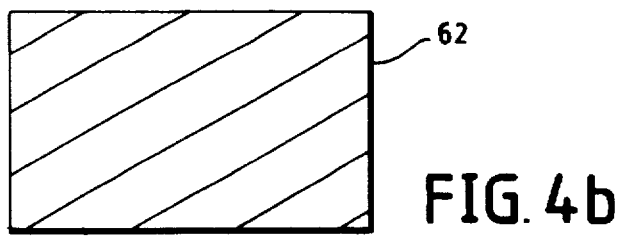

In FIG. 4a, an incident beam of illumination 54 is shown illuminating facet 44 at the critical angle when no sample is in place. Normal to facet 44 is shown the entrance pupil 56 of video camera 26. Again, evanescent field 52 is shown extending beyond facet 44. Without a sample, the incoming beam 54 is totally internally reflected from facet 44 where it is directed as a beam 58 along the indicated path to emerge from facet 60. Since no light enters entrance pupil 56 under these conditions, the image displayed on monitor 22 is completely dark as shown in FIG. 4b at 62.

Figure 4C:
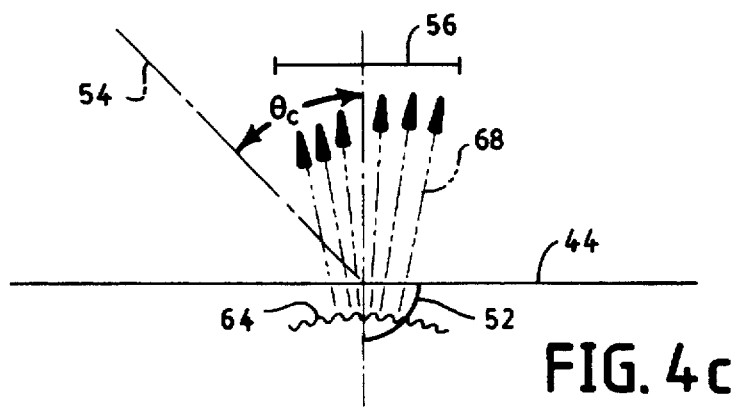
Figure 4D:
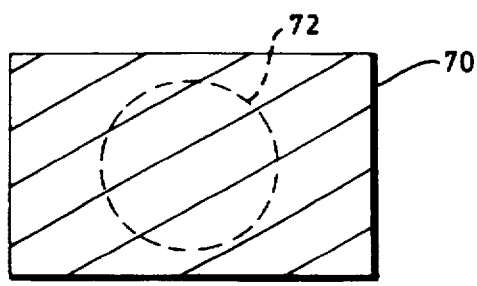

The conditions that prevail when a sample is brought into contact with evanescent field 52 are illustrated in FIG. 4c. Here, a sample 64 with a scattering surface, such as a rough surface, interrupts evanescent field 52 to scatter illumination 68 into entrance pupil 56 where it is used to form an image of the sample surface. The intensity of the scattered radiation, which has been converted from bound energy at the surface of facet 44 to propagating radiation in body 34, depends on the local scattering properties and the local depth of penetration of the sample's microtopographic features. The resultant image displayed on monitor 22 is shown in FIG. 4d where it can be seen that an image area 72 is displayed against an otherwise dark field. Hence the name "dark field" photon tunneling imaging. Because the signal is measured with respect to a dark field, this invention provides generally advantageous signal to noise ratios.

In practice, a sample, like 64, is brought into contact with evanescent field 52 with a three-axis, micro manipulable translation stage 72 such as is shown in FIG. 2. Here, a sample 74 is shown sandwiched between facet 44 and the surface of stage 72.

Experience has shown that the intensity of propagating radiation converted from the evanescent field can be high enough to visualize and measure surface details ranging from between less than a few angstroms to about 10 micrometers. Useful signal may also be generated with this illumination system to image both reflecting and transmissive materials.

Figure 3:
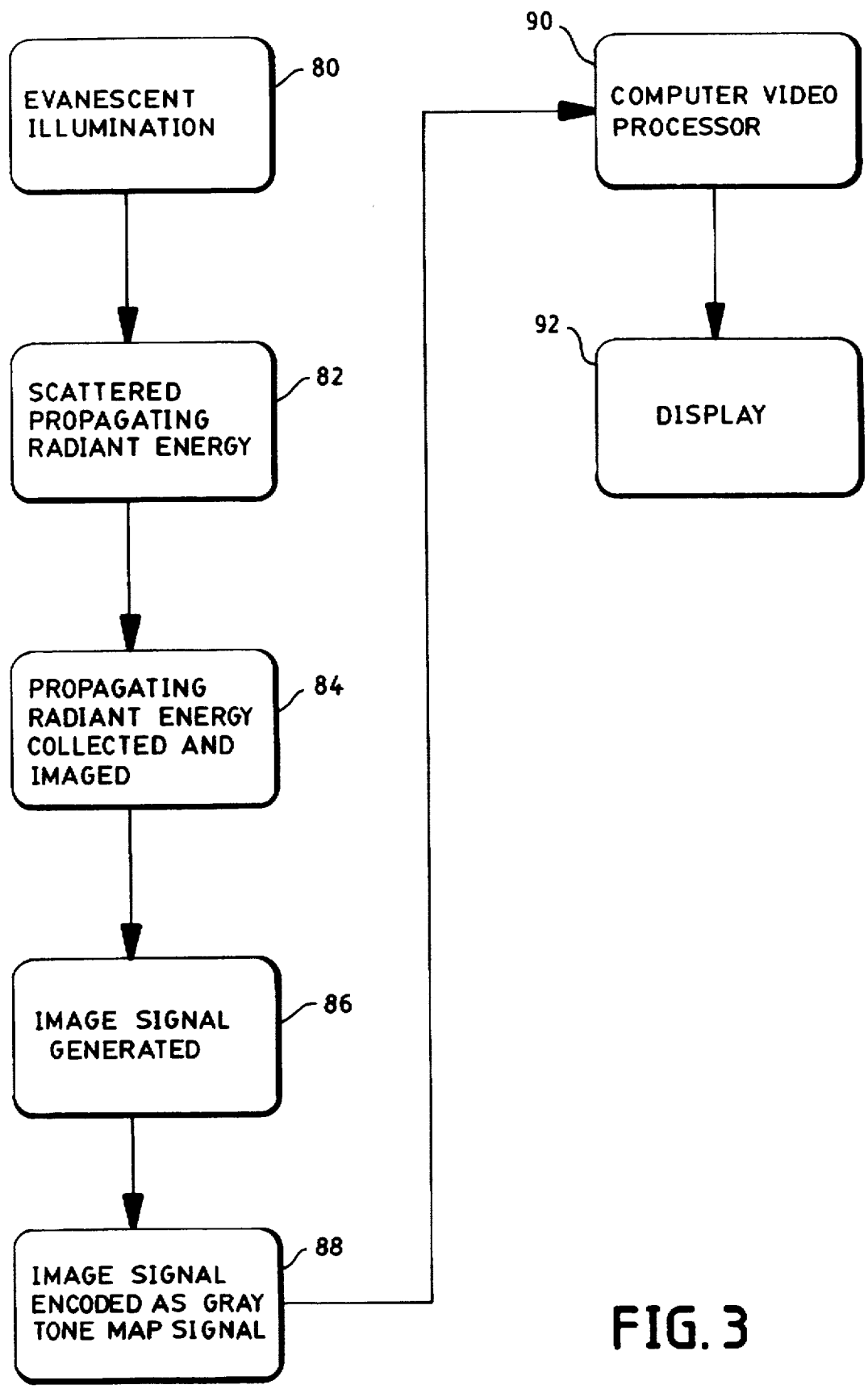
FIG. 3 is a flow chart illustrating the operation of various embodiments of the invention.

FIG. 3 is a general flow chart for the operation of imaging system 10 as well as other embodiments to be described. As shown there, first an evanescent field is formed at a suitable measuring interface as indicated at block 80. Radiation from the bound evanescent field is converted by scattering and proximity into propagating radiation at block 82. The intensity of the propagating radiation depends on the local scattering properties and local depth of penetration of the sample surface into the evanescent field. Following at block 84, the propagating radiant energy is collected and imaged onto a photo detector as by the CCD of video camera 26. An image signal is then generated in block 86 and the intensity of the image signal varies in accordance with the microtopographic features of the sample under scrutiny. The image signal from block 86 is encoded as a gray tone map signal in which gray tones represent feature dimensions. This may be via a look-up table (LUT). The gray tone map signal is then formatted for 2D and 3D display via a computer or other suitable video signal processor at block 90. The formatted signal is then displayed at block 92 with monitor 22 or other suitable display as will be subsequently described.

The dark field imaging system of the invention is seen to be complementary to the usual photon tunneling microscope (PTM) of the prior art in that scattering surfaces such as paper are difficult to view in the normal PTM because the scatter competes with the gray scale tunneling image, while a smooth surface that is viewed easily with PTM will be largely invisible in dark field PTM because the image in the latter is formed by what is scattered out of the evanescent field, which is very little for such a smooth surface. Another important observation is that in FIG. 4a for the dark field PTM, the entrance pupil 56 is clear of the incident illumination in the dark field PTM, whereas the entrance pupil is the same as the exit pupil for the illumination in the photon tunneling microscope. This separation or decoupling of the illumination and imaging optics in the dark field PTM allows much more freedom in control of the illumination to maximize, for example, the vertical tunneling range that is the sensible amplitude of the exponentially decaying evanescent field, or to control polarization more easily so that non-dielectric samples may be viewed.

It should be reiterated at this point that the extent of similarity of dark field PTM to a normal dark field optical microscope ends with the representation of a sample as bright against a dark background, in that the light illuminating a sample in the latter is not evanescent, but is rather the usual propagating electromagnetic field. Therefore, no resolution enhancement is enjoyed in the lateral plane. Nor is there any relation between height and gray scale that only comes with the use of evanescent illumination. Rather, brightness of an object depends on its scattering geometry that includes slope and spatial lateral size, for example.

Figure 5:
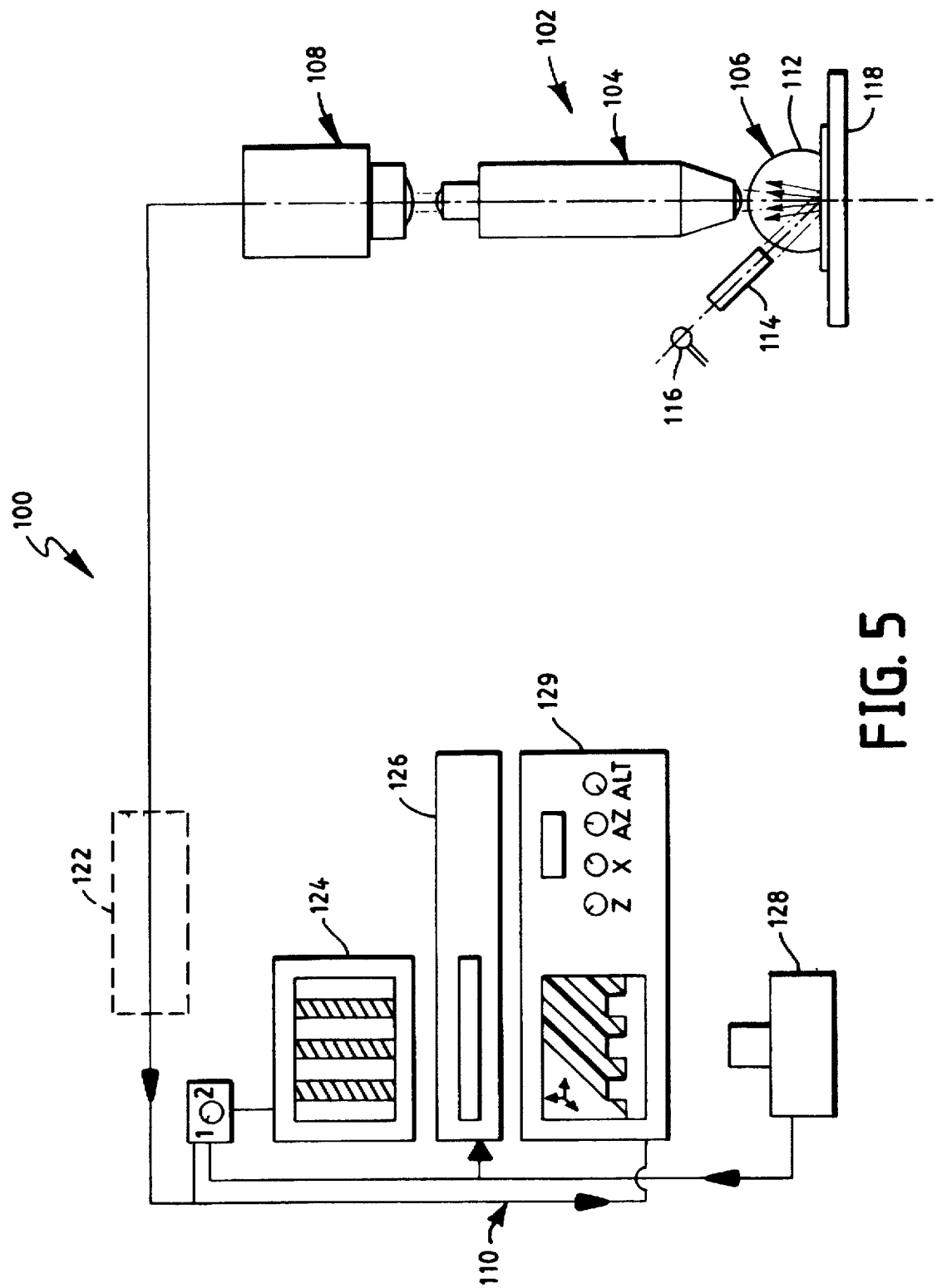
FIG. 5 is a diagrammatic view of an alternate embodiment of the invention in which a microscope is used to view through an aplanatic sphere to image scattered light.
Figure 6:
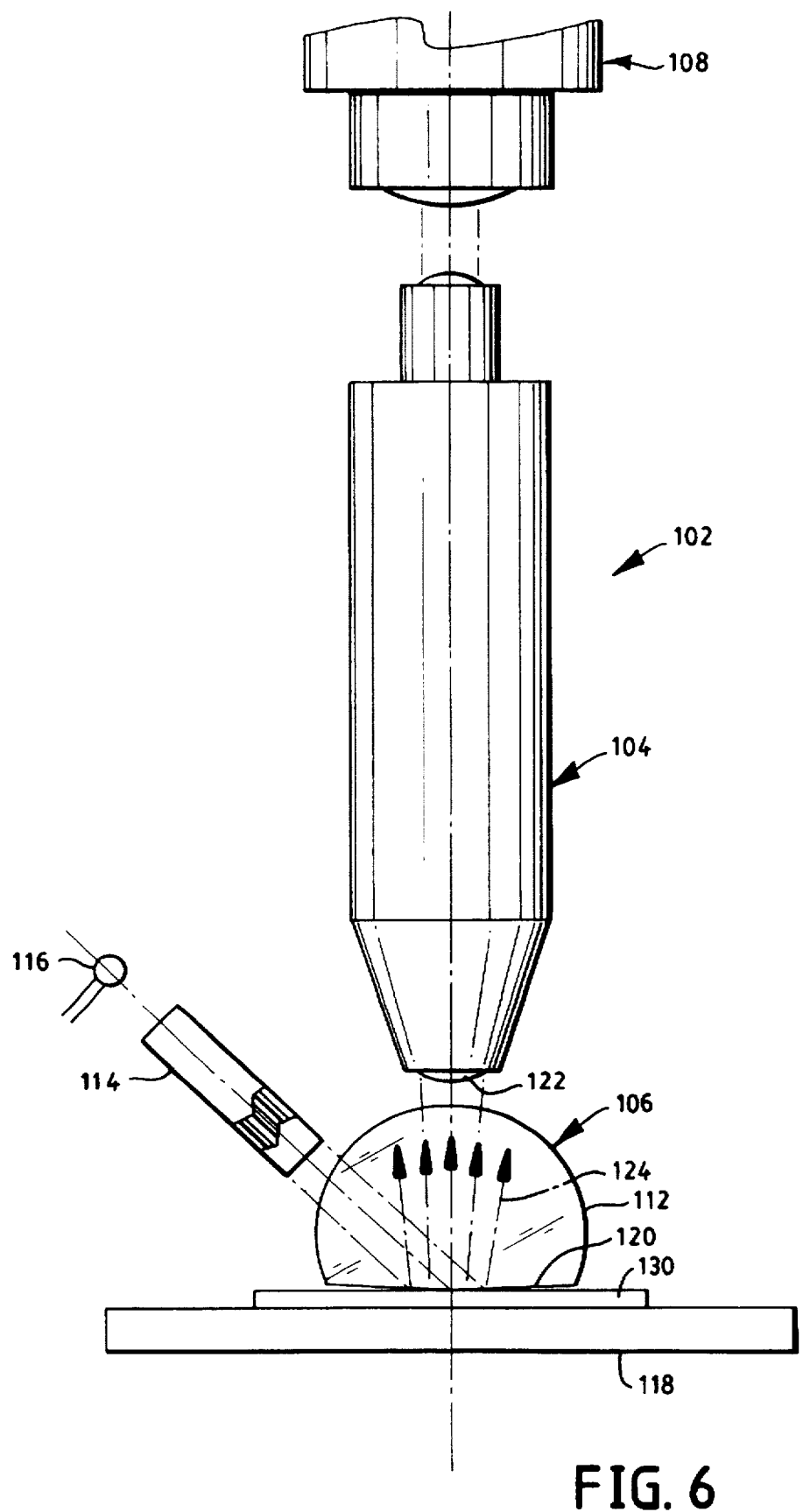
FIG. 6 is a diagrammatic, enlarged elevational view of a portion of the embodiment shown in FIG. 5.

Reference is now made to FIGS. 5 and 6 which illustrate another embodiment for practicing the invention. Here, there is shown generally at 100 a dark field imaging system that comprises an illumination and imaging section 102 and display section 110. Section 102 comprises an optical head 106 which in turn comprises an aplanatic sphere 112 having a slightly curved contact surface 120. Illumination is provided at the critical angle via a fiber optic bundle 116 feed by a source such as a laser, LED, or other solid state device. Suitable radiation controlling filters may also be present in this optical path to control state of polarization or spectral content of illuminating radiation or both.

As before, scattered radiation, such as that indicated at 124, propagates to the entrance pupil of an objective lens 122 of a microscope 104. Microscope 104 is focused through aplanatic lens 106 onto surface 120.

In this manner, microscope 104 forms an enlarged image of a sample and aplanatic sphere 106 may be used to aide in the correction of spherical, coma, and astigmatism aberrations in the usual way.

The image formed by microscope 104 is viewed by a photometric vidicon 108 of conventional design. Vidicon 108 converts the gray scale scattered image into a video signal that is restored by a three-axis oscilloscope 120 to a real-time 3-D image of the sample micro topography while controlling perspective. Other peripherals include a video image processor 122, a VCR 126, a 2D gray scale image display 124, and an XYZ screen video transfer section 128.

An XYZ translation stage 118 is provided for sample positioning as before so that a sample, such as that at 130, can be brought into proximity with the curved surface 120 of aplantic sphere 106. Curved surface 120 facilitates contacting the sample and, as will subsequently be explained, provides other functions.

Previously, the inventive dark field photon tunneling imaging system embodiments were intended to be used in stationary modes of operation with the sample moveable with respect to the optical heads. Because the dark field approach permits decoupling between the illumination and imaging optical paths, other optical head configurations are possible, and these will now be taken up.

Figure 7:
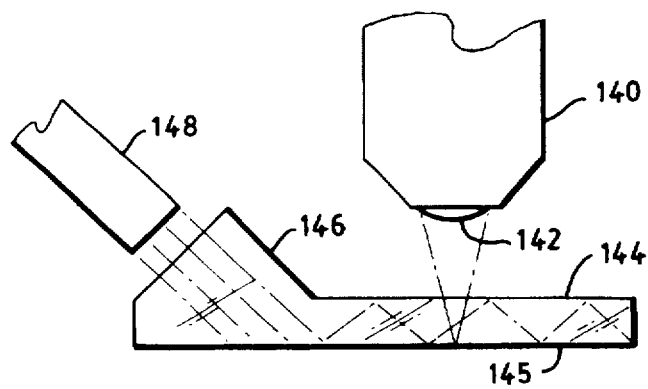
FIGS. 7, 8, and 9 are diagrammatic illustrations in which a decoupled light source, objective, and detector camera are arranged for use in another embodiment of a dark field photon tunneling imaging system according to the invention.

In FIG. 7, an imaging device, a video camera, vidicon, or microscope is equipped with an objective 142. Dark field objective 142, which contains the entrance pupil as shown in FIG. 4a, is made to image through a transmissive dielectric body 144 that corresponds to body 34 in previous figures. A light source 148 is incident on a prism 146 that is coupled optically to slab body 144 so that total internal reflection of the light occurs at least at the distal surface 145 of body 144 so that an evanescent field exists outside of distal surface 145. The sample to be imaged is brought proximal to distal surface 145 so that it is within the evanescent field as was illustrated in FIG. 4c. Although the light source 148 is shown as a unidirectional one, and in some cases this type of illumination is preferable, there are many possible illumination configurations as will be illustrated subsequently.

Figure 8:
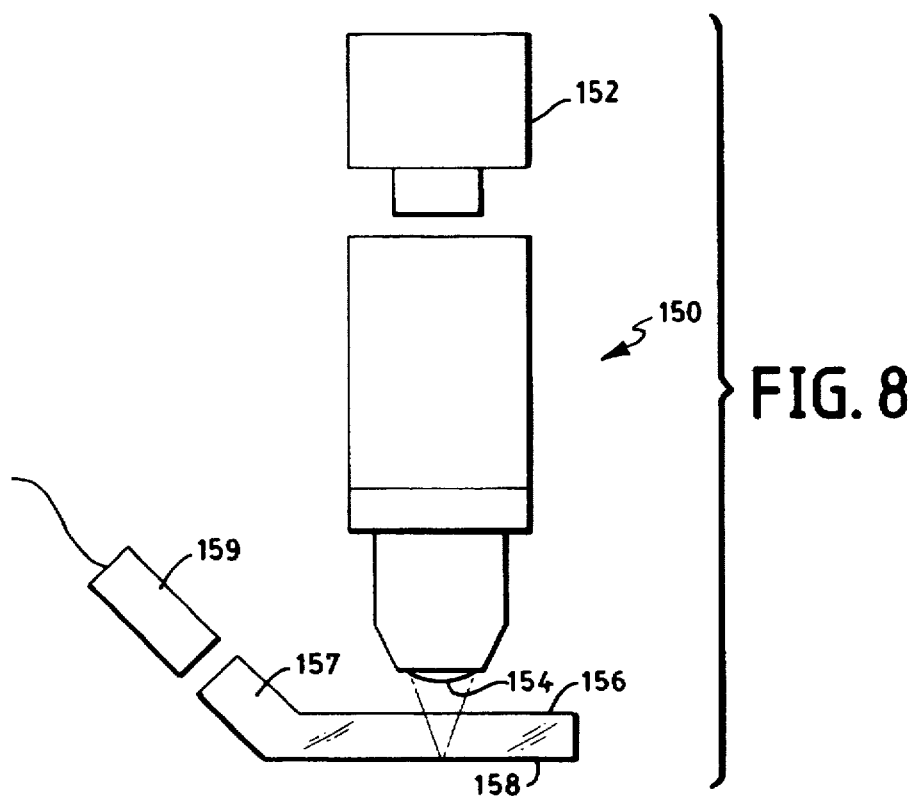

In FIG. 8, a more complete dark field PTM instrument 150 is seen to include, in one configuration, an imaging detector such as a CCD camera 152 onto which the real image from an objective 154 is projected. Alternately, a projection eyepiece can be included in this arrangement for increased magnification, and objective 154 can even be a zoom of variable magnification. Illumination is provided via a totally internally reflecting slab block 156 where the evanescent field is formed at a distal end 158. A source 159 is coupled to body 156 via a bent up section 157.

Figure 9:
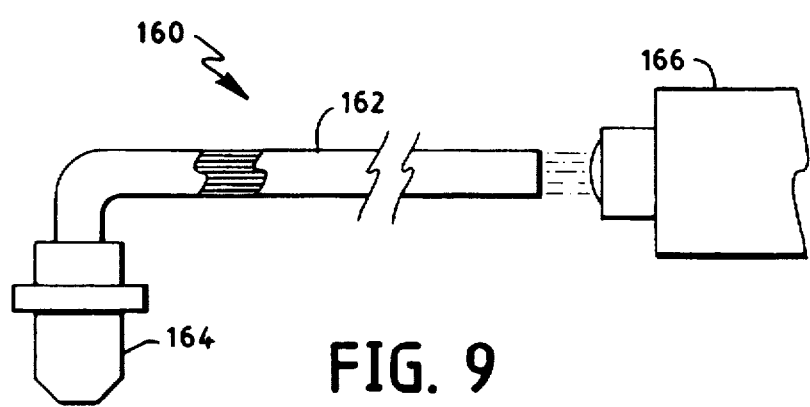

Another useful configuration in shown in FIG. 9. Here, a system 160 uses a coherent imaging fiber optic bundle 162 to relay the image formed by an objective lens 164 to a remote camera and illumination source 166. This embodiment is particularly suitable for use in tight and otherwise inaccessible spaces.

A number of additional illumination configurations are possible, as illustrated in FIGS. 10 through 24, and each offers its own unique advantages. The common element in all of these variations is that total reflection of the illumination is made to occur at least at the distal surface of the body in order to cause the necessary evanescent field illumination outside of and adjacent to the distal surface.

Figure 10:
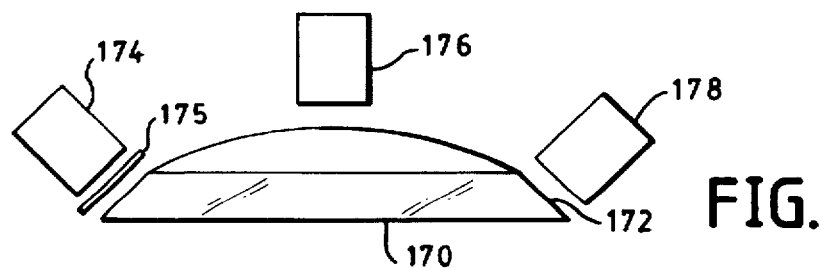
FIGS. 10 through 24 are diagrammatic views illustrating variations of transmissive body geometries that can be used as the total internal reflection element for the invention.

In FIG. 10, a transmissive body assembly 170 in the form of a figure of rotation provides the optical head functions of previous embodiments. Body assembly 170 includes angled incident entrance facet 172 that extends around its circumference. This allows several, or more than one, discrete light sources (174, 176, and 178) to be placed at any azimuthal angle about the axis of rotation. It should be understood that "light source" or lighting means as used in this disclosure can be a laser diode, a light emitting diode (LED), a fiber bundle carrying light from a remote source, incandescent, halogen, or other light source. At plane 175 can be placed a polarizing filter, wavelength filter, phase plate, or other light controlling device.

Figure 11:
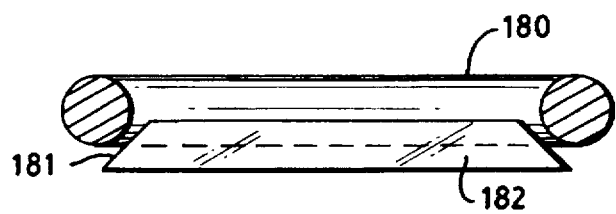

In FIG. 11, the discrete light sources of FIG. 10 are replaced with an annular light bulb source 180 for lighting the angled circumferential edges 181 of an annular slab block 182 to illuminate the sample from all directions.

Figure 12:
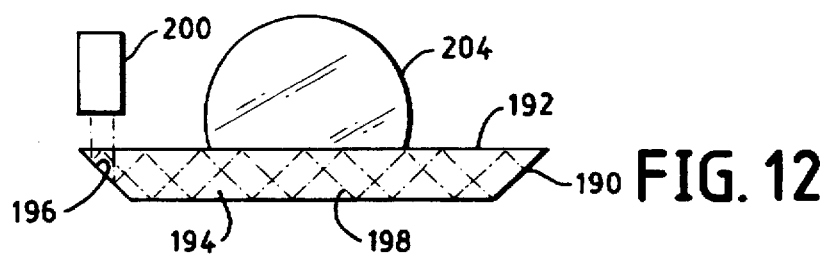
Figure 13:
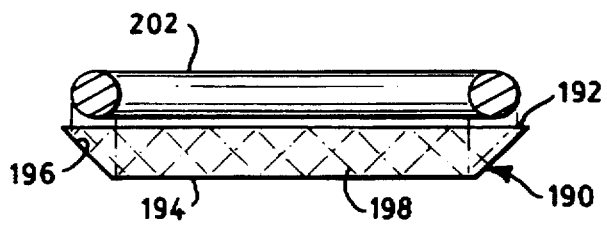

In FIGS. 12 and 13, light from a source is incident normal to the surface 192 of a body 190 that is parallel to the distal surface 194 but is totally internally reflected by angled edge surface 196 so that it undergoes multiple total internal reflections 198. The light source can be discrete as at 200 or tubular as at 202.

In FIG. 12, an optional truncated or "aplanatic" sphere 204 may be made integral with the flat plate 190 in order to improve the image according to aplanatic principles.

Figure 14:
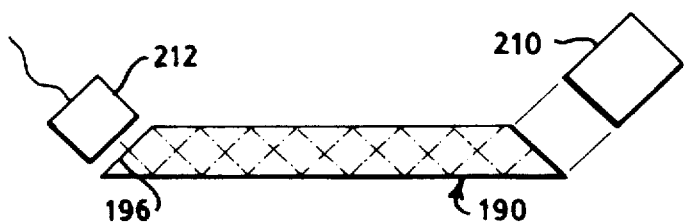

In FIG. 14, the light source is a monochromater 210 so that analytical dark field PTM can be done. An optional detector 212 is shown at the exit face 196 of the body 190 which is now inverted. The main detector here would still be an imaging camera that is not shown here but elsewhere.

Figure 15:
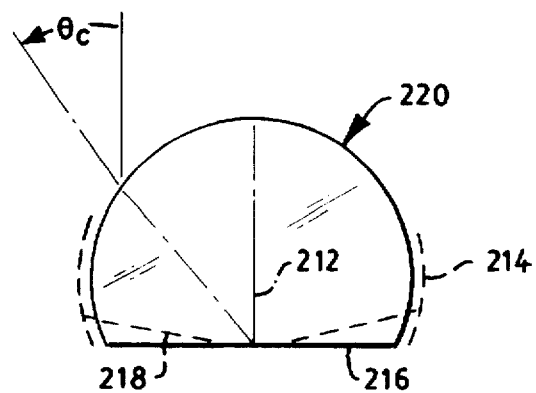

An additional illumination embodiment is illustrated in FIG. 15. As with the embodiments seen previously, the embodiment discussed here would serve as the optical head. In FIG. 15, the transmissive body is in the form of an aplanatic sphere 220 that is truncated at an optically prescribed center thickness 212 such that the image through aplanatic sphere 220 is improved over a parallel flat plate by being aplanatic. The illumination is incident to sphere 220 at angles equal to and greater than the critical angle $\theta_c$. The dotted lines 214 indicate an optional metallic coating, the purpose of which is to allow the incident light to enter the sphere at other angles. Surface 216 is the total reflection surface from which the evanescent field emanates. The dotted radius 218 indicates a preferred curved surface to facilitate proximity between the aplanatic sphere and the sample (which is not shown), and also to facilitate sliding of the aplanatic sphere along the sample in the XY plane. The slight curvature does not effect the optical quality of the image to any significant degree, and yet greatly simplifies the practical use of this aplanatic sphere.

Figure 16:
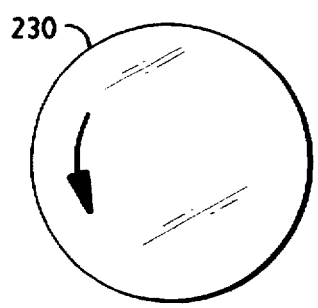

A complete sphere 230 is shown in FIG. 16. While the imaging quality of a completely spherical transmissive body is not as good as the aplanatic sphere or even the flat plate bodies, it is acceptable for certain applications where a rolling optical probe is needed. The spherical geometry allows for rolling contact with the sample, analogous to the tip of a ball point pen. This embodiment is beneficial where sliding contact between the transmissive body and the sample are undesirable.

Figure 17:
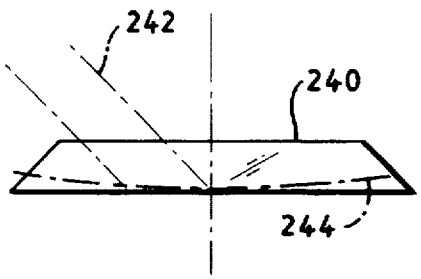

FIG. 17 shows a rotated solid Dove prism 240 with a curved distal surface indicated by the dotted radius line 244 in comparison to a flat distal surface, with curvature again to facilitate contact with the sample and aid in sliding over the sample in the XY plane. This curvature, the radius of which can be measured and known, also may serve to calibrate height to gray scale in the photon tunneling scattered image. Light enters the Dove prism as a beam 242 as shown.

Figure 18:
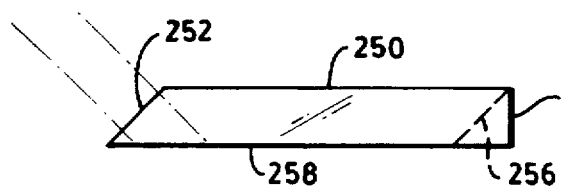

FIG. 18 shows another variation of a transmissive body that is a normal Dove prism 250 except that opposing the incident entrance plane 252 is a truncated plane 254 perpendicular to the distal surface 256, or as indicated by the dotted line 256, parallel to the face 252. This geometry affords advantages in some analytical applications, such as spectroscopic.

In FIGS. 19 through 23, the transmissive body is a very thin plate which serves to guide the light that is launched into it at and beyond the critical angle with multiple total internal reflections. It should be understood that in all of these embodiments, the means of launching the light into the light guide can be a single unidirectional means as shown, or a multitude of discrete like means, or a continuous figure of rotation of the means shown for omnidirectional illumination, analogous to the illumination schemes discussed earlier. The advantage common to all of these embodiments is that an objective, such as that shown at 270 in FIG. 23 can now have a very small working distance and higher numerical aperture, thus affording higher lateral resolution and a wider range of magnifications and fields of view, as well as affording a much more compact device overall. As with the other embodiments, it is understood that these thin plate waveguides can substitute for the transmissive slab body assemblies.

Figure 19:
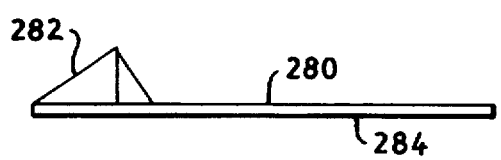

In FIG. 19, the means of launching light into a waveguide 280 is a prism 282 optically coupled to waveguide 280, so that light incident to prism 282 is at or beyond the critical angle and so undergoes multiple total internal reflections within waveguide 280, giving rise to evanescent field illumination at the distal surface 284.

Figure 20:

In FIG. 20, the means of launching light into a waveguide 290 is a set of micro prisms 292. This set of micro prisms 292 could also be in the form of periodic microstructure known as diffractive optics.

Figure 21:
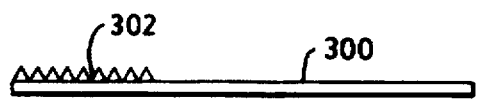

In FIG. 21, the means of launching light into a waveguide 300 is a holographic optical element, or HOE 302.

Figure 22:

In FIG. 22, a waveguide 310 is flexible, and the means of launching light into the flexible waveguide 310 can be a prism 312, HOE, diffractive optics (kinoform), or micro prisms.

Figure 23A:
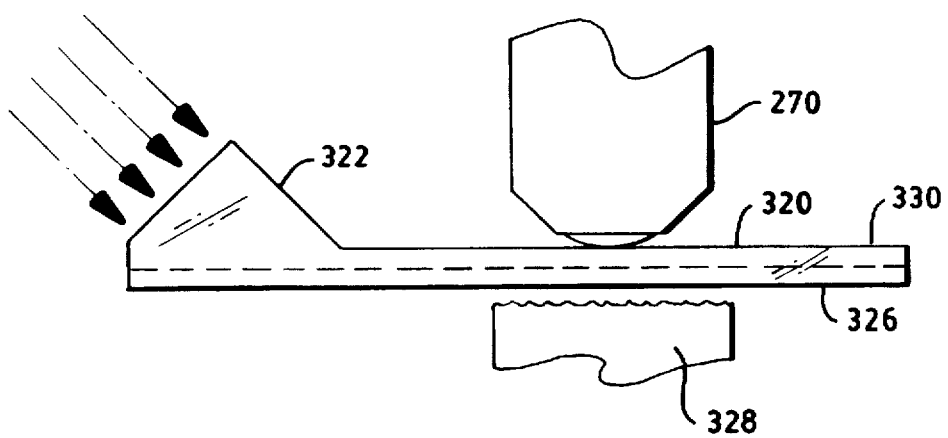
Figure 23B:
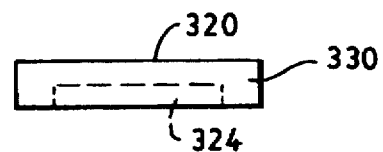

In FIG. 23a and 23b, a waveguide 320 has lower refractive index core 320 in which the total internal reflections occur. Core 324 is exposed on the distal side 326 directly to the sample 328, while the cladding 330 above core 324 maintains total reflection in the event of external contacting material.

It will be appreciated that a thin transmissive parallel plate or flexible membrane may be used to contact to the distal surface of any of the above transmissive bodies and act as a disposable protective covering. If damaged during sliding contact with the sample, it is removed and replaced, so that expensive damage to the main distal surface is avoided.

Also, the distal end may be coated in well-known ways with a hard anti-abrasive coating such as diamond.

Although not shown, all of the transmissive body embodiments discussed above and shown can have a metallized distal surface, with the thickness of the metallization chosen for the illumination wavelength and the incident angle such that a plasmon field is excited on the metal layer by the evanescent field. Therefore, all of the foregoing bodies can be used for surface plasmon microscopy, with all the benefits that brings to, for example, fluorescence microscopy.

Similarly, all of the transmissive bodies discussed above can have multiple dielectric thin film coatings on their distal surfaces in order to cause optical resonance, such that the amplitude of the evanescent field is increased for better signal to noise, and better vertical resolution.

Also, the entrance and exit faces of the transmissive bodies can be coated and arranged geometrically so that the transmissive body becomes a cavity resonator.

Figure 24:
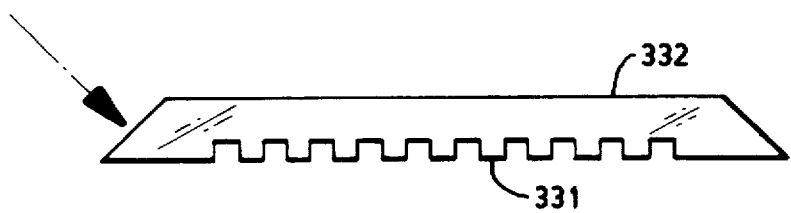

And finally, all of the distal surfaces can have non-smooth surfaces, where the random or periodic surface structure has a spatial period smaller than the wavelength of the illuminating light in order to generate a diffraction-born evanescent field for even higher lateral resolution such as with the diffraction grating 330 formed in a transmissive body 332 shown in FIG. 24.

In FIGS. 25 through 33, several ways of mounting and using the dark field photon tunneling imaging system are illustrated. The many embodiments of the illumination and transmissive bodies discussed above can be used and combined with the mountings to be described.

Figure 25A:
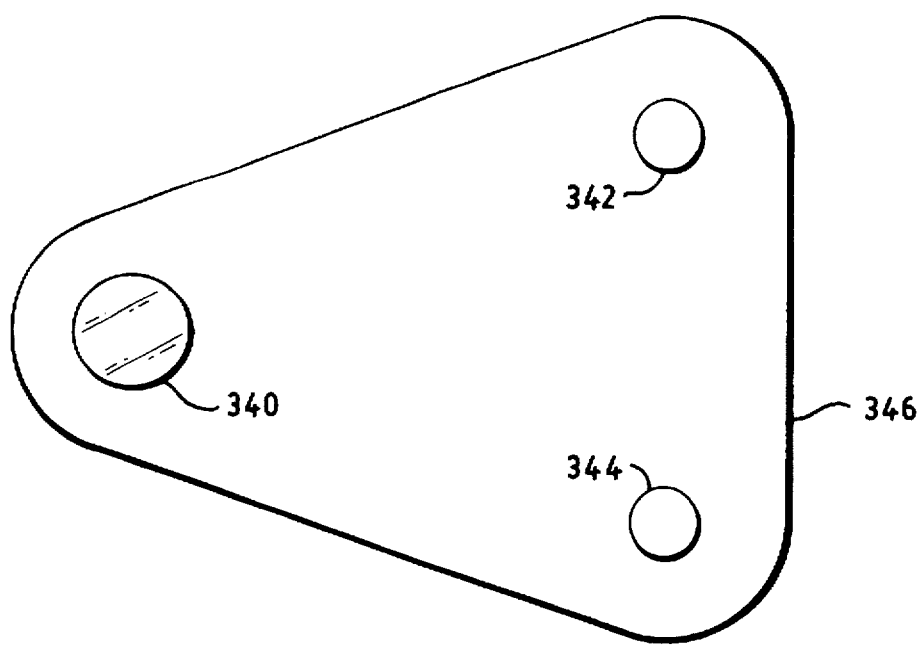
FIGS. 25 through 30 are diagrammatic views of mounting arrangements in which the imaging section a dark field photon tunneling system comprises one pod in a three pod kinematic base for a portable surface profiler.

In FIG. 25a, the transmissive body is shown at 340 as one of three pods, the other two being shown at 342 and 344. All three pods are arranged in kinematic fashion on a baseplate 346 such that when baseplate 346 is placed on a reasonably flat sample surface, the distal surface of the transmissive body 340 is automatically in contact with the sample surface, in focus, and aligned. In this way, the dark field PTM functions ergonomically less like a traditional microscope and more as a computer "mouse", except that is a powerful surface profiler. This compact, portable device is easily placed on an airplane wing, or production web of paper, or painted hood of an automobile, for example.

Figure 25B:
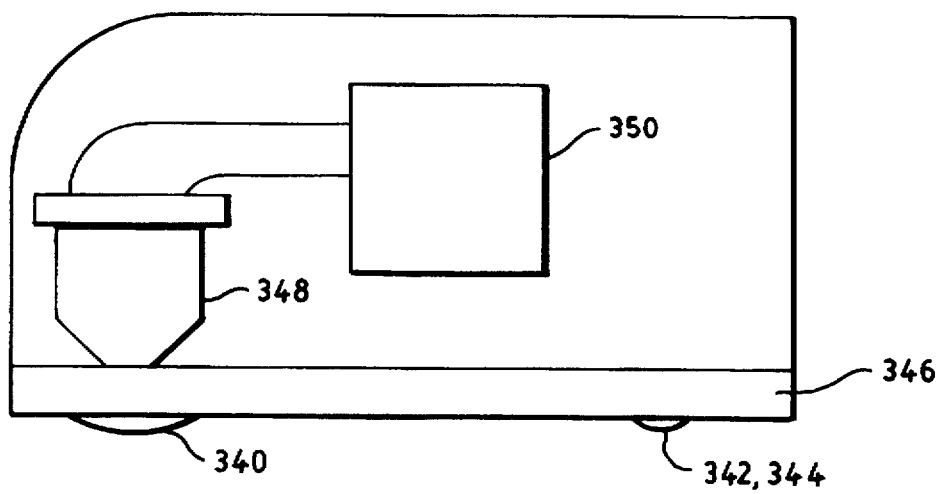

In FIG. 25b, the baseplate and pods are shown in profile with the rest of the dark field photon tunneling imaging system components mounted to the baseplate. These include an imaging and illumination section 348 and a control section 350. Imaging and illumination section 348 and control section 350 operate in a manner similar to the embodiment 160 of FIG. 9.

Many mechanical and other features can be incorporated into the baseplate 346 to provide devices with different capabilities depending on the specific visualization or measurement tasks. Although they will described and shown individually in what follows, the features can in many cases be combined.

Figure 26:
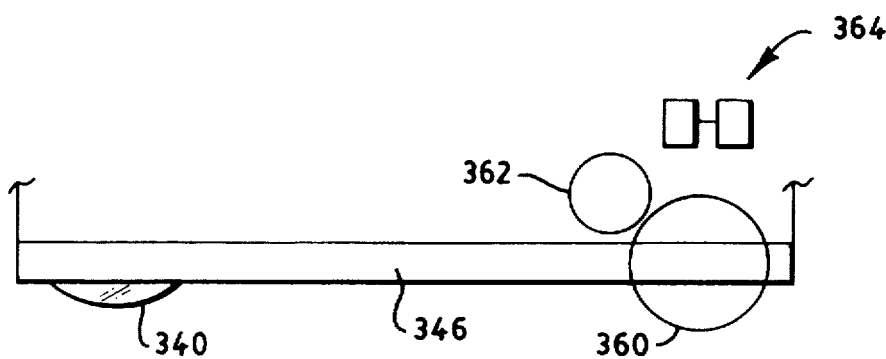

In FIG. 26, two non-optical pods 360 are motor driven wheels or balls, with one means of drive indicated by motors 362 and 364. The baseplate 346 can then be driven about the sample surface.

Figure 27:
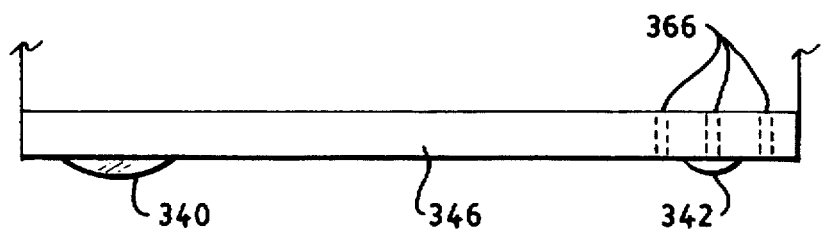

In FIG. 27, means for air bearing levitation 366 are incorporated into or around all three pods (340, 342, and 344). The air pressure can be used not only for frictionless movement about the sample, but can also control the separation between the distal surface of transmissive body 340 and the sample, and with differential control over any two pods, alignment of the optical axis normal to the sample surface is achieved (this is important on non-flat sample surfaces).

Figure 28:
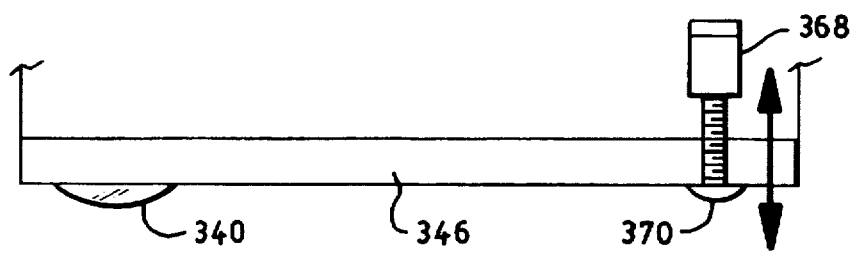

In FIG. 28, two of the pods (only one shown at 370) are mechanically adjustable in height with micrometers 368 or piezo drives to similarly adjust alignment on non-flat surfaces.

Figure 29:
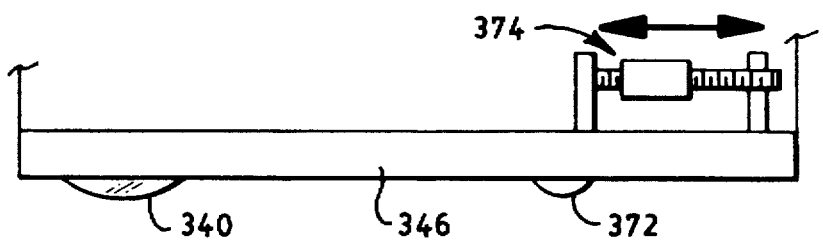

In FIG. 29, a counterbalance weight 374 is added such that the two non-optical pods (only one shown at 372) are at the fulcrum point of the device. Sliding weight 374 toward or away from the fulcrum point adjusts the amount of gravity loading of the transmissive body 340 against the sample.

Figure 30:
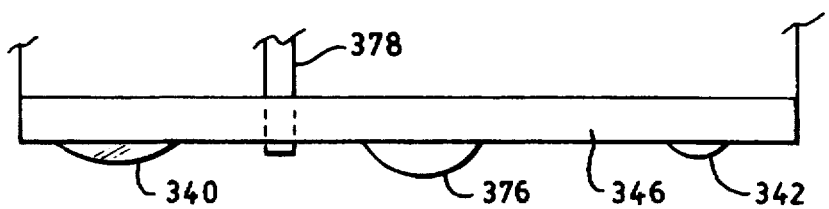

In FIG. 30, a computer "mouse-like" feature is incorporated into the baseplate 346 so that the position and movement of baseplate 346 and the imaging and illumination sections may be indicated in a well-known manner on a computer screen. For this purpose a ball 376 and well-known positioning technology may be incorporated into baseplate 346. Also in FIG. 30, a marker 378 is added to baseplate 346 so that areas of interest, or defective areas, can be marked in industrial applications. Marker 378 may be any of well-known types such as an inking device.

Figure 31:
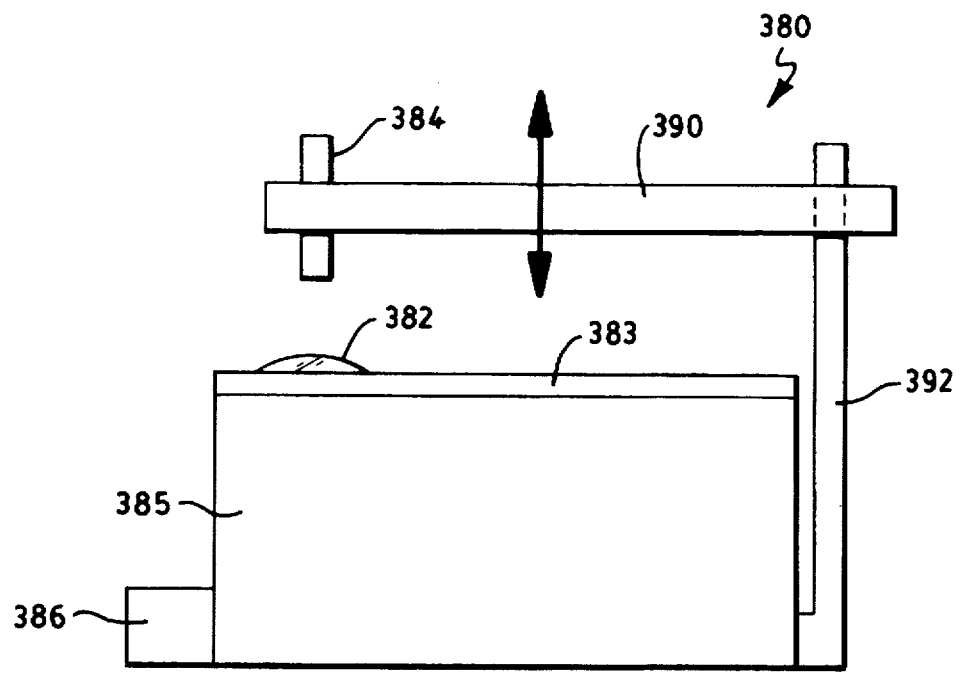
FIG. 31 is a diagrammatic illustration of a viewing section of a dark field photon tunneling system that has been inverted to form yet another embodiment of the invention.

As seen in FIG. 31, the dark field photon tunneling imaging system is very convenient to use also in an inverted position, where a transmissive body distal surface 382 is facing upward. The operator can then hand-place a sample onto the distal surface 382 for immediate images of the sample topography and very rapid throughput of samples. In FIG. 31, an inverted system designated at 380 is accomplished by combination of the portable base 383 similar to the one discussed above nested in a receiver base 385 that has, for example, an optional port for a monochrometer 386 for spectral analysis in addition to topographic profilometry. An optional arm 390 is shown that serves to apply loading to the sample with a device 384 that is an air jet, spring loaded piston, or other mechanism for that purpose. Arm 390 may be raised and lowered into position via a column 392. Other useful, but optional features not shown, are means for heating or cooling the transducer pod and sample, or incorporation of patterning of the illumination for manipulation of microscopic particles.

Figure 32A:
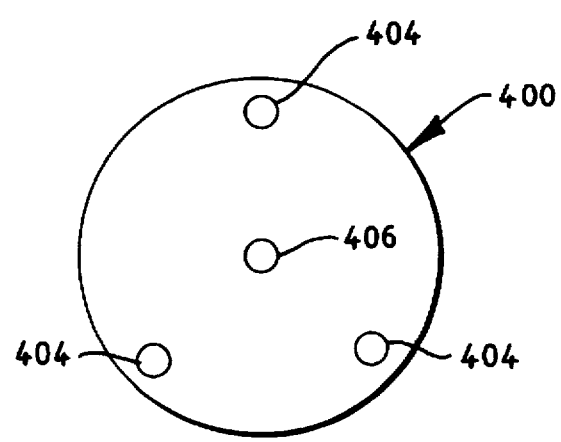
FIGS. 32a–32c are diagrammatic views showing a dark field photon tunneling microscope mounted as a spring-loaded piston in the center of a kinematic three point ring, in both an inverted as well as upright configuration.
Figure 32B:
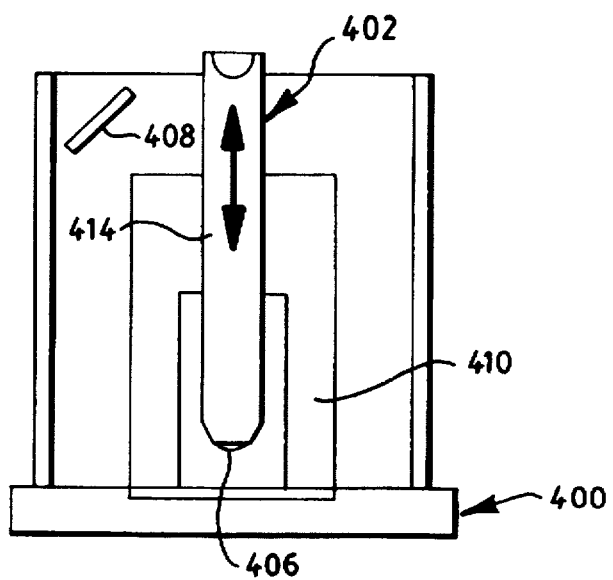
Figure 32C:
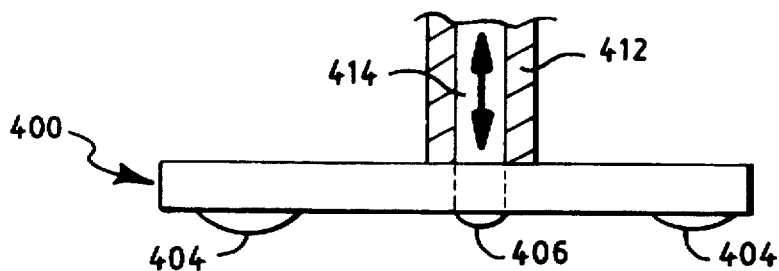

Another useful mounting for a dark field photon tunneling imaging system is seen in FIGS. 32*a–c*. Here, an imager 402 is mounted as a spring loaded piston 414 within a base 400 having three equally spaced pods or balls 404, as is found in an optical spherometer. The distal surface 406 of the transmissive body automatically contacts a flat or curved sample placed on the three pods 404. Piston 414 is mounted in a bored out block 404 in which there is placed a spring 412. In optical fabrication, this mounting configuration provides the optician with both the radius of curvature of the optical surface as well as the roughness statistics and topography, and the degree of optical polish. This configuration can also be used in a downward orientation, as in the center of the base described previously with pods 404 contacting the surface along with the piston 414.

Figure 33:
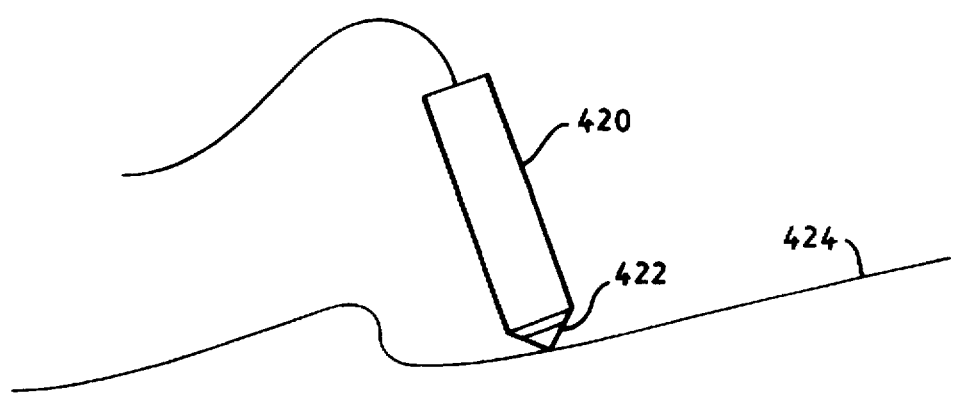
FIG. 33 is a diagrammatic illustration of a dark field photon tunneling microscope configured and used as a hand-held device that is placed in contact with the sample.

In FIG. 33, the dark field photon tunneling imaging and illumination sections are configured as a hand-held probe 420, with the distal surface of the transmissive body 422 placed against the sample 424.

Figure 34:
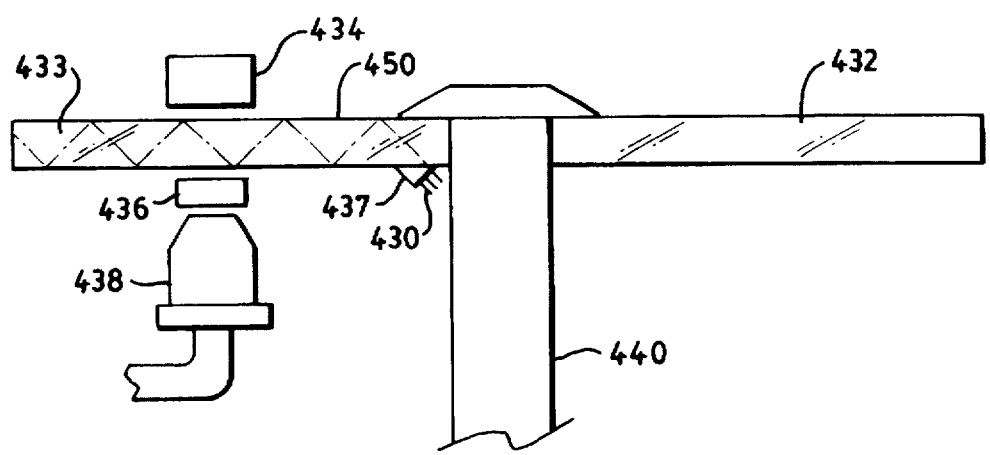
FIG. 34 is a diagrammatic illustration of the dark field photon tunneling technique applied to measuring flying height of a magnetic data recording head in a typical drive arrangement for floppy or rigid disk magnetic media.

The dark field photon tunneling invention can be applied to measure flying height of magnetic read-write heads above floppy or rigid disks in the standard test drives, such as Guzik™, used in the industry. In FIG. 34, light 430 is launched into a glass or polycarbonate analog disk 432 so that it undergoes multiple total internal reflections 433 and therefore induces an evanescent field at both glass to air interfaces. Any of the launch methods previously discussed can be used for this application. Alternately, the edge of disk 432 can be chamfered to form an integral prism face, or can be molded with this prism face to begin with. Even a scattering surface on this edge will launch light into disk 432, though less efficiently and with less control over incident angle. An inside edge 437, nearest to a spindle hub 440, is shown and is the preferred light launch site, but even the outer edge of the disk 432 can serve as the launch site. As a real read/write head (434 or 436) approaches the disk surface 450, it is illuminated by the evanescent field, which is converted into propagating light via scatter by the head, rather than by refraction as in the optical proximity device or photon tunneling microscope. The scattered light enters the dark field PTM objective 438. The typical light-colored ceramic heads will scatter the best, but with a more sensitive detector other less scattering heads may be measured as well. The unadorned glass (or other material) disk will work. However, performance may be improved by blackening, metallization, anti-reflection, or high-low stack dielectric coatings that are selectively applied to strategic areas of the disc or head to improve image contrast and signal to noise, such as one or both of the disk surfaces, or the inside or outside rim of the disk. In addition, a magnetic coating may be added if optically transmissive enough to view through (the near infra-red wavelengths transmit best through such magnetic coatings). Also, a planar waveguide may be created in the disk surface facing the head by infusing chemicals to alter the refractive index. The advantages of using the dark field photon tunneling are all those of photon tunneling but, in addition, the viewing axis is normal to the disk and head surface, thereby eliminating the need for additional optics to view at the critical angle. In addition, it will be understood that it is preferable in the measurement of flying heights with head arrangements for double sided media, it is best to use one real head and one transparent head so the full aerodynamic environment of the read/write system is experienced.

Figure 35:
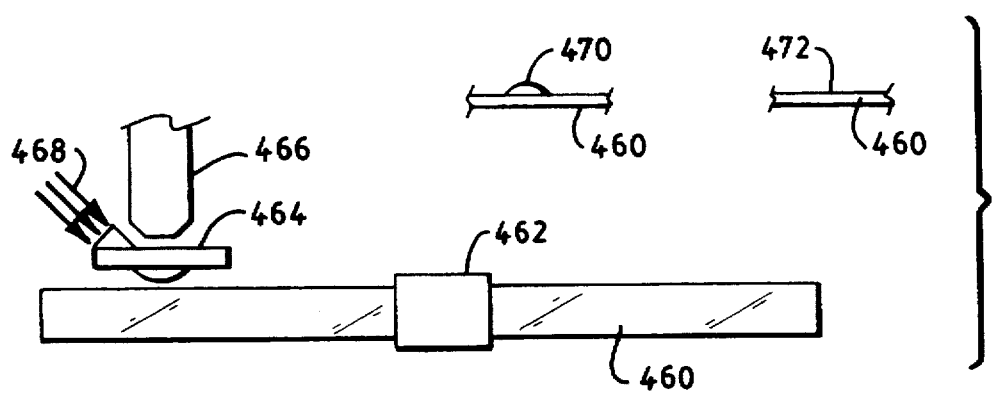
FIG. 35 is a diagrammatic illustration of a dark field photon tunneling technique applied to high resolution writing and reading of optical data in an optical data drive.

Referring now to FIG. 35, it can be seen that dark field photon tunneling, with its high resolution characteristics, can be applied with advantage to the field of optical data storage and retrieval. In FIG. 35, a rotating polycarbonate or other similar optical compact disc 460, or a similar optical card scanned in the XY plane, contains data bits in the form of optical scatter sites 138 on or very near the surface, or nanometer-high topographic bumps 470 on the surface, either of which the evanescent field is sensitive to. These scattering sites may be formed in any well-known way such as by laser writing to form pits, local index changes, or the like. A flying total internal reflection head 464 and 468, that can be configured as previously described, serves to illuminate disc 460 in evanescent field light. This same evanescent field light and total internal reflection head can be used to write scatter sites in addition to reading them. In this way, the high resolution of the evanescent field is used to advantage to create scatter sites of smaller sizes, so that the storage density increases. In reading mode, the information bits convert the evanescent field to scattered light that an objective 466 receives. To achieve this, low flying heights are required for the evanescent field to illuminate the encoded information. While flying heights of a fraction of a micron are attained even now in the industry, such low heights cause slower data access times to avoid crashing the head into the disk. Alternately, the scatter sites or bumps can be internal to the disk. Into the surface of the disk may be formed a HOE, kinoform, or micro prisms such that, when illuminated normal to the disk surface, only the local area below each element of the micro prism or equivalent HOE is illuminated with evanescent light. In this way, the flying height not restricted by the reach of the evanescent field, and can be quite large, for fast data access and crash-free operation. The submicron proximity of the recording layer to the evanescent field is integral to the media, which is the disk with integral microprisms, HOE, or kinoform. In addition to HOE, kinoform, and microprisms, which cause an evanescent field by refraction of the illumination beyond the critical angle, the evanescent field can be caused by diffraction with a diffraction grating integral to the disk, which grating has a period that is smaller than the wavelength of the illumination.

Because there is no metallization as in current optical data disks, this optical data invention can be more archival in that it is not subject to corrosive decay of the metallized layer. The optical data bits can be index or phase changes induced in a material that can also be erased (e.g., phase change material) with alternate procedures of exposure and annealing with the same light source, by varying exposure time. Alternately, the optical data bits can be actual bumps. Materials such as semiconductor doped glasses, chalcogenide glasses, as well as many available photopolymers, which exhibit topographic swelling with exposure to propagating light, also do the same with exposure by evanescent fields.

The optical data bits can be placed within the disk at different distances from its surface, thereby generating different intensities as they interact more of less with the evanescent field. This can be used to advantage to add a third dimension to the optical encoding algorithm, thereby greatly increasing the storage density of the disk. This increased storage density can be used for additional information storage or for redundant storage of information set to reduce access time and error rate to provide extremely robust storage systems. One form of this is to place the information bits in a plurality of high and low index stacks for layers so that each high-low interface supports and evanescent field. Each high-low layer pair is an information channel which can be selected by varying the light source incident angle, phase, polarization, or wavelength.

Figure 36:
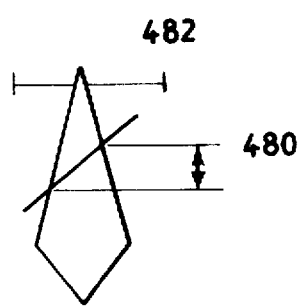
FIG. 36 is a diagrammatic view showing how the coupled imaging and illumination optics of a typical photon tunneling microscope can be modified for dark field photon tunneling microscopy.

As illustrated in FIG. 36, the benefits of dark field photon tunneling imaging or microscopy can be enjoyed in a normal photon tunneling microscope through the use of a conversion which restricts the useful NA of the objective to less than 1.0, and also by reducing the level of specular illumination. Both of these expediencies, while not completely necessary, enhance the performance for dark field purposes. Here, a stop 480 is placed in the epi-illumination path to only allow illumination from numerical aperture 1 to the full extent of the objective, usually 1.25. A complementary annular mask 482 is placed in the imaging optical path to mask out light returning at a numerical aperture greater than one, thus assuring the collection of primarily scattered light from a sample.

Figure 37:
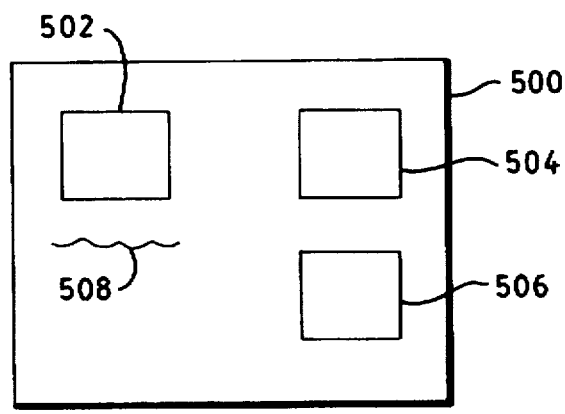
FIGS. 37 and 38 show representative displays of 3-D and gray scale images, profilometry, and roughness statistics such as are available from the dark field photon tunneling microscope.
Figure 38:
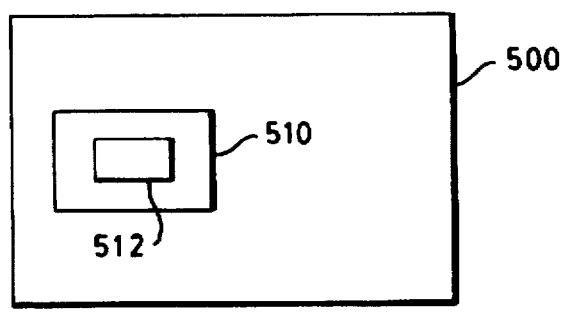

Reference is now made to FIGS. 37 and 38 which show generally at 500 the viewable area of a monitor or other display device. Within the viewable area, it is possible using well-known techniques to provide different widows to display analytical data, such as statistical data, about the properties of a surface along with image of the surface. For example, box 502 could contain autocorrelation information, 504 could be the image, box 506 and enlargement of the image, and line 508 the surface profile. Similarly, boxes with this type of numerical and graphical or pictorial information can be displayed within boxes as box 512 is within box 510 in FIG. 38.

The dark field photon tunneling imaging systems of the present invention operate in a novel way because detected light has been scattered out of the evanescent light field by the sample surface. As a result, the advantages of this invention are: increased tunneling range, increased topographic sensing, ability to look at thick and opaque samples, ability to look at rougher surfaces, less sensitivity to optical inhomogeneity in the sample, decoupling of imaging and illumination optics for greater freedom to control illumination and imaging characteristics. Further advantages are real time high speed imaging, and high energy throughput that facilitates optical analytical techniques.

It will be understood that the present invention is by no means limited to the particular constructions and methods herein disclosed and/or shown in the drawings, but also comprises any modifications or equivalents within the scope of the claims.

What is claimed is:

1. A dark field, photon tunneling imaging system for optical storage and retrieval, said system comprising:

a light transmissive recording medium comprising a surface having formed therein a plurality of local optical scattering sites by which information has been encoded proximate said surface;

a flying total internal reflection head comprising a total internal reflection surface, said total internal reflection surface positioned proximate said recording medium surface;

lighting means for illuminating said total internal reflection head such that an evanescent field is produced at said total internal reflection surface, said evanescent field extending to said recording medium surface;

means for mounting said light transmissive recording media so that said scattering sites are brought into contact with said evanescent field so that light initially bound within said wavelength evanescent field is converted at least in part into propagating light through the process of back scattering from said scattering sites such that, in the absence of a scattering site or where a scattering site is distant, no evanescent light energy is converted into propagating light, said propagating light varying in correspondence with the scattering properties of said scattering sites and the local distance of said scattering sites from said evanescent field;

imaging means positioned to collect said propagating light and form an image with it in which the scattering sites are present as imagewise variations in image intensity; and photodetector means for generating an image signal having an amplitude that varies in accordance with the presence or absence of a scattering site.

2. The system of claim 1 further including means for receiving said image signal and generating a tone mapping signal in which said scattering sites are encoded as imagewise variations in tone.

3. The system of claim 1 in which said light transmissive recording media is a circular disk.

4. The system of claim 3 wherein said light transmissive recording media is mounted for rotation.

5. The system of claim 1 wherein said imaging means comprises a microscope.

6. The system of claim 1 wherein said lighting means comprise a light source and coupling means for introducing light into said transmissive recording media by which said evanescent field is formed.

7. The system 6 wherein said coupling means comprises an annular prism.

8. The system of claim 6 wherein said coupling means comprises a holographic optical element (HOE) formed in the surface of said light transmissive recording media.

9. The system of claim 6 wherein said coupling means comprises a kinoform formed in the surface of said light transmissive recording media.

10. The system of claim 6 wherein said coupling means comprises microprisms formed in the surface of said light transmissive recording media.

11. The system of claim 6 wherein said coupling means comprises a diffraction grating proximate the surface of said light transmissive recording media where the grating period is less than the wavelength of illumination to crate said evanescent field.

12. The system of claim 1 wherein said lighting means and said imaging means have optical paths that are optically uncoupled with respect to one another.

13. The system of claim 1 wherein said lighting means comprises a collimated light emitting diode.

14. The system of claim 1 wherein said lighting means comprises a laser diode.

15. The system of claim 1 wherein said lighting means comprises an incandescent lamp.

16. The system of claim 1 wherein said lighting means comprises a discrete source and a fiber optic bundle coupled to said discrete source.

17. The system of claim 1 wherein said light transmissive recording media is rectangular in form.

18. The system of claim 1 wherein said scattering sites are on the surface of said light transmissive recording media.

19. The system of claim 1 wherein said scattering sites on internal to the volume of said light transmissive recording media.

20. The system of claim 19 wherein said scattering sites are different distances from the surface of said light transmissive recording media to enhance the number of degrees of encoding.

21. The system of claim 20 wherein said light transmissive recording comprises a plurality of layers of different index of refraction and wherein said scattering sites reside within said layers.

22. The system of claim 21 wherein the information encoded in said layers is selected by varying the illumination wavelength, incident angle, polarization, or phase.

23. The system of claim 1 wherein said scattering sites are formed by said lighting means.

24. The system of claim 1 wherein said scattering sites are phase changes in a dielectric or semiconductor.

25. The system of claim 1 wherein said scattering sites are bumps in semiconductor-doped, chalcogenide glasses, or photopolymer.

26. The system of claim 1 wherein said scattering sites are writeable and eraseable by the process of altering the power and exposure time of said illumination.

27. A dark field, photon tunneling method for decoding optically stored information, said method comprising the steps of:

mounting a light transmissive recording medium comprising a recording surface in which information has been stored in the form of selectively placed microscopic scattering sites;

illuminating said recording surface of said light transmissive recording media with a wavelength evanescent field by means of a flying total internal reflection head so that light initially bound within said wavelength evanescent field is converted at least in part into propagating light through the process of back scattering from said scattering sites of said recording surface such that, in the absence of a scattering site or if a scattering site is distant, no evanescent light energy is converted into propagating light, said propagating light varying in correspondence with the presence or absence of a scattering site and the proximity of a scattering site to said evanescent field;

collecting said propagating light and forming an image with it in which the presence or absence of a scattering site is decoded as an imagewise variations in image intensity; and detecting and generating an image signal having an amplitude that varies in accordance with said image intensity and image position.

28. The method of claim 27 further including the step of receiving said image signal and generating a tone mapping signal in which the presence or absence of a scattering site is encoded as an imagewise variation in tone.

* * * * *